United States Patent [19]

Talley

[11] Patent Number: 4,533,767

[45] Date of Patent: Aug. 6, 1985

[54] CATALYTIC HYDRODEALKYLATION OF ALKYLATED PHENOLS

[75] Inventor: John J. Talley, Clifton Park, N.Y.

[73] Assignee: General Electric Company, Schenectady, N.Y.

[21] Appl. No.: 606,438

[22] Filed: May 3, 1984

[51] Int. Cl.$^3$ .................... C07C 37/50; C07C 37/48
[52] U.S. Cl. .................................. 568/805; 568/780
[58] Field of Search ..................... 568/805, 780, 716

[56] References Cited

U.S. PATENT DOCUMENTS

| | | | |
|---|---|---|---|
| 3,998,892 | 12/1976 | Leach | 568/805 |
| 4,060,560 | 11/1977 | Leach | 568/805 |
| 4,071,566 | 1/1978 | Leach | 568/805 |
| 4,110,253 | 8/1978 | Leach | 568/805 |
| 4,191,844 | 3/1980 | Bjornson | 568/805 |
| 4,230,895 | 10/1980 | Daly | 568/805 |
| 4,230,896 | 10/1980 | Daly | 568/805 |

OTHER PUBLICATIONS

Francis P. Daly, Journal of Catalysis 61 (1980) 528–532.
Jelinek, "Chemical Abstract", vol. 55 (1961), p. 7357.

*Primary Examiner*—Werren B. Lone
*Attorney, Agent, or Firm*—Richard J. Traverso; James C. Davis, Jr.; James Magee, Jr.

[57] ABSTRACT

Selective catalytic steam dealkylation of ortho- and para-positions of alkylated phenols is accomplished by reacting ortho- and/or para-alkylated phenols with steam in the presence of a catalyst comprised of magnesium oxide, optionally manganese oxide and optionally an organic binder; said reaction may preferably takes place in the presence of an oxidizing atmosphere to extend catalyst life. High degrees of conversion are obtained without loss of the hydroxyl radical of the alkylated phenols.

25 Claims, No Drawings

CATALYTIC HYDRODEALKYLATION OF ALKYLATED PHENOLS

BACKGROUND OF THE INVENTION

This invention relates to a method for dealkylating alkyl phenols. More particularly, this invention is directed to a method for dealkylating ortho- and para-alkylated phenols with steam in the presence of a magnesium oxide catalyst.

It is often desirable to dealkylate the alkylated phenols obtained from coal tars from coal liquifaction processes to provide more valuable products, such as phenol. In addition, it is often desirable to dealkylate 2,4,6-trimethylphenol (TMP), a coproduct in the synthesis of 2,6-xylenol, to more useful alkylated phenols and phenol. These include p-cresol, o-cresol, 2,6-xylenol, 2,4-xylenol and the like.

Methods of dealkylating alkylated phenols are known to the art. These methods include thermal dealkylation, thermal hydrodealkylation and catalytic hydrodealkylation. Thermal dealkylation involves exposing dealkylated phenols to high temperatures (about 800° C.) to achieve thermal cracking of the alkylated phenol and yield phenol. However, this process is not selective and a substantial amount of dehydroxylation occurs under these conditions, producing the less valuable benzene and alkyl-substituted benzene species, as is shown more particularly by Daly in *Journal of Catalysis* 61, 528 (1980), the contents of which are incorporated herein by reference.

Thermal hydrodealkylation of alkylated phenols involves exposing the alkylated phenols to high temperatures in the presence of steam or hydrogen or both, as is shown by Daly in U.S. Pat. No. 4,230,895. This process also causes a significant amount of dehydroxylation, which is undesirable since dehydroxylation produces less valuable products.

Catalytic hydrodealkylation is typically more selective than the processes described above and causes less dehydroxylation. Daly describes a process in U.S. Pat. No. 4,230,896 wherein alkylated phenols are reacted with steam in the presence of a catalyst comprised of a hydrous carrier, a deactivation suppressor and at least one promoter. Catalysts included within those described by Daly include platinum and palladium on alumina and mixtures of palladium and chromium oxide on alumina. A catalytic hydrodealkylation process which reacts alkylated phenols with hydrogen is described by Bjornson in U.S. Pat. No. 4,191,844. This reaction takes place in the presence of a catalyst consisting essentially of magnesium oxide and a Group IIA metal oxide such as manganese oxide. Although these catalytic hydrodealkylation processes are more selective and cause less dehydroxylation than thermal hydrodealkylation, there still remains room for improvement. For example, the percentage of alkylated phenol converted to a new material is very low (about 40%) in the process described in U.S. Pat. No. 4,230,896 and dehydroxylation is still significant, providing 5–30 weight % dehydroxylated products. When the alkylated phenols are reacted with hydrogen in the process described by Bjornson, the rate of dehydroxylation is also high producing large quantities of dehydroxylated products (up to 50 weight %) at high rates of dealkylation. In addition, these processes which utilize a catalyst to dealkylate alkylated phenols are handicapped by the short lifetime of the catalyst due to coking. The catalyst must be reactivated or regenerated periodically and a deactivation suppressant is often necessary.

The catalytic hydrodealkylation process comprising this invention provides high conversion rates with essentially no loss of hydroxyl radicals from dehydroxylation. In addition, the catalyst lifetime is extended for particular embodiments of this invention so as to reduce the frequency of regeneration.

SUMMARY OF THE INVENTION

A method of dealkylating ortho-alkylated and para-alkylated phenols with substantially no dehydroxylation is provided comprising reacting an alkylated phenol with steam in the presence of a catalyst comprising magnesium oxide, said alkylated phenols having at least one alkyl radical of from 1 to 6 carbon atoms either ortho-positioned or para-positioned to the hydroxyl radical. The reaction can optionally take place in the presence of air to extend the life of the magnesium oxide catalyst and the catalyst may optionally contain manganese oxide and/or a binder.

OBJECTS OF THE INVENTION

An object of the invention is to dealkylate alkylated phenols with substantially no loss of hydroxyl radicals.

Another object of the present invention is to dealkylate alkylated phenols at a high conversion rate without loss of selectivity.

Another object of the present invention is decrease the frequency at which the catalyst must be regenerated when dealkylating alkylated phenols by a catalytic steam dealkylation process.

DETAILED DESCRIPTION OF THE PREFERRED EMBODIMENT

The present invention is directed to a catalytic steam dealkylation process which selectively dealkylates the ortho- and para-positions with respect to the hydroxyl radical of an alkylated phenol. The term "dealkylation" as used herein refers to the removal of alkyl groups containing 1 to 6 carbon atoms from the aromatic nucleus of phenols. The term "dehydroxylation", as used herein, refers to the loss of the hydroxyl radical on the aromatic nucleus of the alkylated phenols. The process comprising this invention dealkylates alkylated phenols with essentially no dehydroxylation.

Suitable alkylated phenols which can be dealkylated by this process include those containing one hydroxyl radical and at least one alkyl group at an ortho- or para-position relative to said hydroxyl radical. These alkylated phenols may contain multiple alkyl groups at multiple positions on the aromatic nucleus and these alkyl groups may be straight or branch chained. Examples of suitable alkylated phenols include ortho-cresol, para-cresol and isomers of xylenol, ethyl phenol, n-proylphenol, etc.; which contain at least one alkyl substituent on a para- or ortho-position with respect to the hydroxyl radical. More particularly these include ortho-cresol, para-cresol, 2,4-xylenol, 2,3-xylenol, 2,5-xylenol, 2,6-xylenol, 2,3,4-trimethylphenol, 2,3,5-trimethylphenol, 2,3,6-trimethylphenol, 2,4,6-trimethylphenol, 2,4,5-trimethylphenol, 3,4,5-trimethylphenol, 2-ethylphenol, 4-ethylphenol, 2,4-diethylphenol, etc. The feed of alkylated phenols may be comprised of one single alkylated phenol or a mixture of alkylated phenols; mixtures typically being derived from tar acids obtained from coal liquifaction processes.

The alkylated phenols of the reactor feed may be dissolved in an organic solvent so as to make addition into the reactor easier. Any organic solvent which is inert under dealkylation conditions is suitable, provided it is a good solvent medium for the alkylated phenols. The preferred solvent is benzene. Other suitable solvents include tetrahydrofuran, chlorobenzene, hexane, etc.

The reactor feed also contains steam, either saturated, unsaturated or superheated. The molar ratio of steam to alkylated phenol may be at any value and still provide dealkylation; but preferably, the molar ratio of steam/alkylated phenol falls within the range of about 0.5:1 to about 100:1. The most preferred range of molar ratios for steam/alkylated phenol falls within the range of about 1:1 to 5:1.

The reaction between the alkylated phenol and steam takes place in the presence of a catalyst comprised of magnesium oxide. Any catalytic form of magnesium oxide is suitable for use in this process. It is preferable that the magnesium oxide within said catalyst fall within the range of about 80–90% by weight and that said catalyst be free of oxide compounds which tend to be acidic in nature; such as aluminum oxide, silicon dioxide, silica-alumina, acidic clays, etc. However small quantities of these materials can be tolerated if they are fired to a temperature where they have become inert. As such, they may be used as a support for the magnesium oxide without detrimental effect. Oxides of metals which are basic in nature, as is magnesium oxide, when present in minor proportions, have a promoting action which increases the activity of magnesium oxide, even though these "basic oxides", when used alone, do not have the reactivity or selectivity which magnesium oxide catalysts exhibit. Examples of such promoters include, manganese oxide, zinc oxide, lead oxide, etc. These promoters can be used as a heterogeneous mixture throughout the catalyst bed, coprecipitated with magnesium oxide or placed in separate zones in the reactor. If utilized, they are preferably not present in an excess of 10 weight % of the total catalyst. Where manganese oxide is used, the most preferred range is about 2 to 5 weight % of the total catalyst.

These catalysts may have an inert organic or inorganic binder mixed within in order to permit them to be pelletized and easily handled in the process. Such binders may preferably comprise up to about 20 weight % of said catalyst. Suitable organic binders include: polyphenylene oxide, graphite, etc. Silica is an example of a suitable inorganic binder. Polyphenylene oxide binders are the most preferred.

A suitably porous magnesium oxide catalytic material may be obtained by thermo-decomposition of magnesium carbonate, magnesium hydroxide, or basic magnesium carbonate. Basic magnesium carbonate being a complex of magnesium carbonate, magnesium hydroxide and water having the formula:

XMgCO₃Mg(OH)₂Y(H₂O), where X and Y are whole numbers from about 3 to about 5. If desired, the magnesium compound can be coated on an inert carrier or binder, pelletized and then thermally decomposed to give a porous magnesium oxide coating on the inert substrate. The magnesium compound may be decomposed, i.e., calcined, prior to placement within the reactor or it may be generated from the precursor material within the reactor. It is preferable to calcine the material at about 300° to 500° C. under an atmosphere such as hydrogen gas, nitrogen gas, helium gas, etc.

Magnesium oxide catalysts retain their activity for several days with little loss of specific activity. However, over long periods of operation, carbon deposition (coking) gradually decreases that activity. When this occurs, the catalysts can be regenerated by oxidation of the carbon by passing oxygen or air over the catalyst at temperatures in the range of about 400° to 500° C.

An alternative method utilized to retard the coking of the catalyst surface is to introduce an oxidizing atmosphere (oxygen or air) into the reactor via the reactor feed so that the reaction takes place in the presence of this oxidizing atmosphere, which is preferably air. The preferred volume (flow rate) of oxidizing atmosphere which performs this function provides a value for the mole/hour ratio of oxygen ($O_2$) to alkylated phenol in the range of about 1 to 50. The most preferred values for this ratio fall within the range of 1 to 5. Smaller and larger quantities are also effective and do not inhibit the process from achieving its desired objects and do not cause dehydroxylation. If smaller quantities are used, the catalyst may have to be regenerated.

Air or oxygen will also serve to extend the lifetime of the magnesium oxide catalysts used in transalkylation reactions with alkylated phenols. The utility and function of air in a transalkylation reaction is considered equivalent to its function and utility in a dealkylation reaction over magnesium oxide catalyst. The only distinction being that transalkylation reactions involve the transfer of an alkyl radical to another aromatic nucleus as demonstrated by the following equations:

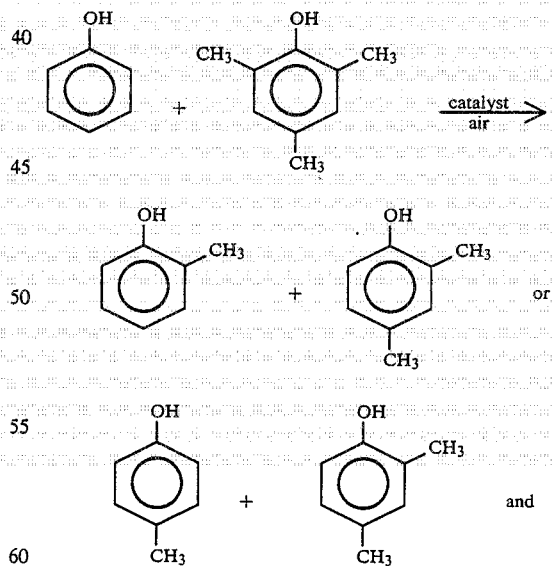

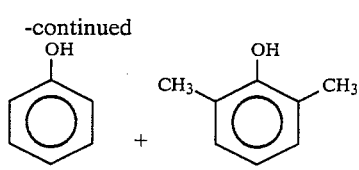

Suitable starting materials and products for transalkylation reactions are much more varied than the examples provided and are similar to those characteristic of dealkylation reactions. For example, the following species may be used in a transalkylation reaction: o-cresol, p-cresol, 2,4-xylenol, 2,6-xylenol, 2,4,6-trimethylphenol, phenol, aromatic amines, such as alkylated anilines and anilines. etc. The alkyl groups may have between 1-6 carbon atoms as with the dealkylation reaction described above. The reactions are ortho and para selective as are the dealkylation reactions, with removal and addition at the ortho position being favored over the para position.

Typical reactor feeds for transalkylation reactions comprise an alkyl radical acceptor, defined herein as a phenol having at least one ortho or para position vacant (phenol) and an alkyl radical donator, defined herein as a phenol with at least one alkyl radical at an ortho or para position (2,4,6-trimethylphenol). A reactor feed may be comprised of one species which satisfies both descriptions, such as o-cresol.

These reactions differ from the dealkylation reactions in that the preferred temperature range is lower, 400°-550° C., and the reactor feed does not contain hydrogen or steam to promote oxidation of the alkyl groups.

The use of a catalyst comprised of about 80-90 weight % magnesium oxide, about 2-5 weight % manganese oxide and about 1 to 20 weight % organic binder, preferably polyphenylene oxide, provides a high degree of conversion of alkyl radical donators, particularly 2,4,6-trimethylphenol in excess phenol. Utilizing air to extend the catalyst lifetime provides a simple and efficient route to producing o-cresol and p-cresol from 2,4,6-trimethylphenol.

The dealkylation reaction proceeds at a temperature within the range of from about 400° to 675° C. with substantially no dehydroxylation at a pressure of about one atmosphere with temperatures within the range of 450° to 550° C. being preferred. These preferred temperature ranges can vary if the reaction takes place at a pressure other than at one atmosphere. At such temperatures, the alkylated phenols in the feed and the dealkylated phenols produced are in vapor form. The reaction proceeds smoothly at atmospheric pressure, which makes it convenient to carry out the process since complex equipment is not required and the hazards which are characteristic of reactions which proceed under pressure are avoided. However, pressures above and below atmospheric pressure can be utilized when desired. The pressure is preferably maintained within the range of about 1 to 50 atmospheres, with pressure at about 1 atmosphere being the most preferred.

The rate at which alkylated phenols are fed into the reactor to react with steam in the presence of catalyst (liquid hourly space velocity) is not critical to achieve the desired objects of this invention. The flow rate of reactants does effect the product yield by determining the amount of contact time between the alkylated phenols, steam and catalyst. Due to the difference in the specific activities of magnesium oxide catalysts, each catalyst will have a different optimum flow rate than another. The more active the catalyst, the shorter contact time necessary to produce the same quantity of dealkylated phenols. Therefore, to obtain a particular conversion rate, higher liquid hourly space velocities can be used with more active catalysts while lower liquid hourly space velocities are necessary with less active catalysts. A flow rate which is too high will flood the catalyst and not permit the reaction to proceed. Where the catalyst utilized contains manganese oxide promotor within the range of about 2 to 5 weight % and an organic binder within the range of about 0 to 20 weight %, a flow rate having a liquid hourly space velocity in the range of about 0.1 to 3.0 grams alkylated phenol/hour/grams of catalyst is preferred. The most preferred flow rate is at a liquid hourly space velocity of about 0.3 to 0.5 grams of alkylated phenol/hour/grams of catalyst. Both higher and lower flow rates can be utilized with such catalysts.

The starting materials are preferably in the vapor phase when in the presence of the magnesium oxide catalyst at the operable temperature ranges. To avoid cooling of the catalyst below the reaction temperature selected, it is preferable to vaporize and preheat the starting materials prior to contact with the magnesium oxide catalyst. To minimize the decomposition of the starting materials, it is most preferable to maintain the starting materials at the minimum temperature necessary to vaporize them and then preheat the starting materials to the reaction temperature immediately prior to contact with the magnesium oxide catalyst. This can be accomplished by passing the vaporized starting materials through a heated tube of metal or quartz or by passing the vaporized starting materials over heated quartz beads just prior to entry into the catalyst bed. It is preferable to utilize the same heating medium to preheat the vapors which is used to heat the catalyst bed so as to maintain a stable reaction temperature within the reactor.

Both products and unreacted starting materials exit the magnesium oxide catalyst bed preferably in vapor form and are typically condensed to a liquid for subsequent use. This can be accomplished by any conventional means, such as common air or water condenser. The products are then separated from the condenser effluent, preferably by distillation in a conventional distillation apparatus.

The process can be carried out in a conventional reactor used for vapor phase reactions over a solid catalyst. For example, a tubular reactor of quartz or metal filled with a static bed of magnesium oxide catalyst is suitable. The reactor is heated to the desired temperature by any conventional means; for example, it can be heated by surrounding the reactor with an electric heater or by surrounding the reactor with a heated gas or liquid. Multiple electric heaters with separate controls permit the catalyst bed temperature to be controlled quite easily, even though the reaction is exothermic.

In order that those skilled in the art may better understand this invention, the following experiments are provided by way of explanation and not by way of limitation.

EXPERIMENTAL

In each of Examples 1 through 52, the following procedure was utilized:

An electrically heated 1 inch by 12 inch quartz tubular reactor was wrapped with three heating tapes and three thermocouples at 6 inch intervals to monitor the temperature along the catalyst bed. The three heating tapes were controlled by three variable transformers such that the temperature of the catalyst bed was controlled to within ±10° C. The quartz tube was packed with 5 ml quartz beads followed by 100 ml of a magnesium oxide catalyst having 2-5 weight % magnesium oxide promotor and 1-20 weight % polyphenylene oxide binder unless indicated otherwise. The last three to four inches of the reactor were packed with quartz beads. The catalyst was calcined at about 450° to 500° C. for three to four hours under a flow of air (0.1 SCFH). The catalyst bed was then brought to the desired temperature. The reactants were introduced at the top of the bed with a metering pump (Eldex Laboratories Model AA-72-S) at a rate which provided a liquid hourly space velocity of about 0.5, unless indicated otherwise. An airflow was maintained throughout all experiments, unless otherwise indicated, at a flow rate between about 0.005 to 0.8 standard cubic feet per hour (SCFH). The products which exited the reactor were condensed and the organic effluent was separated from the water and analyzed by gas chromatography with a Varian Associates Vista 6000 gas chromatograph.

EXAMPLES 1–4

A feedstock of 2,4,6-trimethylphenol and steam was utilized in Examples 1–4. These materials were reacted over a magnesium oxide catalyst containing 2 to 5 weight % magnesium oxide and a polyphenylene oxide organic binder. The weight of 2,4,6-trimethylphenol, weight of steam, the reaction temperature and flow rates of reactants are shown in Table I. The products obtained and the degree of conversion are shown in Table II. No dehydroxylated products were observed.

TABLE I

| Example # | Wt. 2,4,6 TMP* (g) | Wt. H$_2$O (g) | Temp (°C.) | 2,4,6 TMP* Flow Rate (g/min) | H$_2$O Rate Flow (g/min) |
|---|---|---|---|---|---|
| 1 | 10.0 | 5.0 | 500 | ~1.0 | 0.5 |
| 2 | 10.0 | 4.0 | 550 | ~1.25 | 0.5 |
| 3 | 10.0 | 5.0 | 600 | ~1.0 | 0.5 |
| 4 | 15.0 | 5.0 | 600 | ~1.0 | 0.35 |

TABLE II

| Ex. # | Phenol (g) | o-Cresol (g) | p-Cresol (g) | 2,6-Xylenol (g) | 2,4-Xylenol (g) | 2,4,6 TMP* (g) | Conv. (%) |
|---|---|---|---|---|---|---|---|
| 1 | — | — | 1.02 | 3.97 | 17.16 | 76.51 | 23.49 |
| 2 | 0.79 | 2.58 | 4.59 | 3.49 | 25.85 | 60.07 | 39.93 |
| 3 | 6.74 | 6.04 | 12.76 | 4.69 | 26.44 | 40.27 | 59.73 |
| 4 | 1.06 | 2.02 | 2.33 | 3.90 | 18.60 | 70.71 | 29.29 |

*TMP - trimethylphenol

EXAMPLES 5–14

In Examples 5–14 a feedstock of 2,4,6-trimethylphenol and steam was passed over a magnesium oxide catalyst containing no promoters or organic binders. The reaction temperature was maintained between 450° to 600° C. The values for the weight of 2,4,6-trimethylphenol, the weight of steam, the reaction temperature and the flow rates of reactants are shown in Table III. The products obtained and the degree of conversion are shown in Table IV. No dehydroxylated products were observed.

TABLE III

| Example # | Wt. 24.6 TMP* (g) | Wt. H$_2$O (g) | Temp. (°C.) | 2,4,6 TMP* Flow Rate (g/min) | H$_2$O Flow Rate (g/min) |
|---|---|---|---|---|---|
| 5 | 20.0 | 10.0 | 450 | 1.0 | 0.5 |
| 6 | 20.0 | 10.0 | 500 | 1.0 | 0.5 |
| 7 | 20.0 | 10.0 | 500 | 1.0 | 0.5 |
| 8 | 20.0 | 7.0 | 500 | 1.0 | 0.35 |
| 9 | 20.0 | 7.0 | 500 | 1.0 | 0.35 |
| 10 | 20.0 | 10.0 | 550 | 1.0 | 0.5 |
| 11 | 20.0 | 10.0 | 550 | 1.0 | 0.5 |
| 12 | 20.0 | 10.0 | 600 | 1.0 | 0.5 |
| 13 | 20.0 | 10.0 | 600 | 1.0 | 0.5 |
| 14 | 20.0 | 7.0 | 600 | 1.0 | 0.35 |

TABLE IV

| Ex. # | Phenol (g) | o-Cresol (g) | p-Cresol (g) | 2,6-Xylenol (g) | 2,4-Xylenol (g) | 2,4,6 TMP* (g) | Conv. (%) |
|---|---|---|---|---|---|---|---|
| 5 | — | — | — | 0.69 | 4.89 | 93.54 | 6.46 |
| 6 | — | — | — | — | 6.58 | 92.04 | 7.96 |
| 7 | 1.31 | — | — | 2.20 | 8.02 | 87.05 | 12.95 |
| 8 | 0.52 | — | — | 1.40 | 7.16 | 86.27 | 13.73 |
| 9 | — | — | — | 0.59 | 3.32 | 94.68 | 5.32 |
| 10 | 0.23 | 0.93 | 1.15 | 3.42 | 17.32 | 73.01 | 26.99 |
| 11 | — | 1.59 | 3.10 | 4.29 | 25.51 | 63.04 | 36.96 |
| 12 | 2.37 | 4.60 | 9.32 | 5.20 | 31.96 | 41.98 | 58.02 |
| 13 | 1.56 | 2.59 | 6.72 | 3.99 | 29.70 | 51.70 | 48.30 |
| 14 | 2.26 | 1.62 | 2.45 | 4.41 | 22.03 | 64.94 | 35.06 |

*TMP = trimethylphenol

EXAMPLES 15–23

A feedstock comprised of 2,4,6-trimethylphenol in a benzene solution and steam was utilized in Examples 15–23. The volume of the benzene solvent is given in Table V. The feedstock was passed over a manesium oxide catalyst containing 2 to 5 weight percent of a manganese oxide promoter and a polyphenylene oxide organic binder. The reaction temperature was maintained at about 600° C. for each of these examples. The weight of 2,4,6-trimethylphenol, and steam and the flow rates of the starting materials for each of these Examples is shown in Table V. The products obtained and the degree of conversion is shown in Table VI. No dehydroxylated products were observed.

TABLE V

| Example # | Wt. 2,4,6 TMP* (g) | Vol. of C$_6$H$_6$ (mL) | Wt. H$_2$O (g) | Flow 2,4,6 TMP* mL/min | Flow H$_2$O mL/min |
|---|---|---|---|---|---|
| 15 | 3.0 | 15.0 | 15.0 | .35 | .35 |
| 16 | 2.0 | 10.0 | 10.0 | .35 | .35 |
| 17 | 2.0 | 10.0 | 15.0 | .35 | .50 |
| 18 | 2.0 | 10.0 | 20.0 | .35 | .50 |
| 19 | 1.0 | 5.0 | 15.0 | .35 | .50 |
| 20 | 2.0 | 10.0 | 15.0 | .35 | .35 |
| 21 | 2.0 | 10.0 | 15.0 | .35 | .35 |
| 22 | 2.0 | 10.0 | 10.0 | .35 | .35 |
| 23 | 3.0 | 15.0 | 30.0 | .35 | .50 |

TABLE VI

| Ex. # | Phenol (g) | o-Cresol (g) | p-Cresol (g) | 2,6-Xylenol (g) | 2,4-Xylenol (g) | 2,4,6 TMP* (g) | % |
|---|---|---|---|---|---|---|---|
| 15 | 22.98 | 11.53 | 16.22 | 4.24 | 22.15 | 16.61 | 83.39 |
| 16 | 35.13 | 6.89 | 23.51 | 2.46 | 11.98 | 10.38 | 89.62 |
| 17 | 19.69 | 5.98 | 24.09 | 1.93 | 18.72 | 24.72 | 75.28 |
| 18 | 4.74 | 4.98 | 21.12 | 2.07 | 23.07 | 32.15 | 67.85 |
| 19 | 3.40 | 3.38 | 15.58 | 1.82 | 18.84 | 45.84 | 54.16 |

TABLE VI-continued

| Ex. # | Phenol (g) | o-Cresol (g) | p-Cresol (g) | 2,6-Xylenol (g) | 2,4-Xylenol (g) | 2,4,6 TMP* (g) | % |
|---|---|---|---|---|---|---|---|
| 20 | 5.06 | 4.99 | 19.62 | 2.34 | 25.58 | 34.65 | 65.35 |
| 21 | 6.71 | 3.72 | 16.71 | 2.97 | 21.92 | 38.91 | 61.09 |
| 22 | 10.21 | 4.31 | 15.02 | 3.46 | 22.79 | 38.58 | 61.42 |
| 23 | 4.80 | 2.77 | 11.69 | 2.43 | 23.90 | 51.75 | 48.25 |

*TMP = trimethylphenol

EXAMPLES 23-30

A feedstock comprised of 2,4-xylenol in a benzene solution and steam was utilized in Examples 23-30. The ratio of 2,4-xylenol to benzene solvent was 1:1.5. The feedstock concentration was constant in each of the Examples being 10 ml of 2,4-xylenol and 10 ml of steam. The flow rates of 2,4-xylenol and steam were both 0.35 ml per minute. The catalyst utilized in Examples 23-26 comprised a magnesium oxide catalyst containing 2 to 5 weight % manganese oxide promoter and a polyphenylene oxide organic binder. The catalyst in Examples 27-30 comprised a magnesium oxide catalyst without promoter or organic binder. No dehydroxylated products were observed.

TABLE VII

| Ex. # | Temp. °C. | Phenol (g) | o-Cresol (g) | p-Cresol (g) | 2,6-Xylenol (g) | 2,4-Xylenol (g) | 2,4,6 TMP* (g) | Conv. % |
|---|---|---|---|---|---|---|---|---|
| 23 | 450 | 0.92 | 1.47 | 9.05 | 0.61 | 88.27 | 9.40 | 23.39 |
| 24 | 500 | 1.49 | 2.56 | 12.80 | 0.91 | 68.89 | 11.97 | 31.11 |
| 25 | 550 | 2.44 | 3.35 | 15.50 | 1.45 | 60.79 | 12.99 | 39.21 |
| 26 | 600 | 28.55 | 7.93 | 30.69 | 2.27 | 21.89 | 3.74 | 78.11 |
| 27 | 450 | 0.39 | 0.63 | 4.16 | 0.17 | 88.27 | 4.84 | 11.73 |
| 28 | 500 | 0.68 | 0.17 | 7.58 | 0.54 | 82.69 | 6.92 | 17.31 |
| 29 | 550 | 3.09 | 1.91 | 17.18 | 1.67 | 62.57 | 10.63 | 37.43 |
| 30 | 600 | 33.15 | 5.10 | 42.95 | 2.07 | 12.06 | 2.55 | 87.94 |

The temperatures utilized in each Example, the products obtained and the degree of conversion are illustrated in Table VII.

EXAMPLES 31-37

A feedstock utilized in Examples 31-37 comprised 10 ml 2,6-xylenol in a 2,6-xylenol/benzene solution, 1:1.5, and 10 ml of steam. The flow rate for both steam and 2,6-xylenol was 0.35 ml per minute. A magnesium oxide catalyst containing a manganese oxide promoter and polyphenylene oxide organic binder was utilized in Examples 31-34 and a magnesium oxide catalyst without said manganese oxide and polyphenylene oxide binder was utilized in Examples 35-37. Table VIII provides the values for the reaction temperature utilized and illustrates the reaction products obtained along with the degree of conversion. No dehydroxylated products were observed.

TABLE VIII

| Ex. # | Temp. °C. | Phenol (g) | o-Cresol (g) | p-Cresol (g) | 2,6-Xylenol (g) | 2,4-Xylenol (g) | 2,4,6 TMP* (g) | Conv. % |
|---|---|---|---|---|---|---|---|---|
| 31 | 450 | 0.34 | 5.37 | — | 90.73 | 1.12 | 18.86 | 10.27 |
| 32 | 500 | 0.59 | 8.13 | 0.99 | 80.73 | 2.80 | 4.25 | 19.27 |
| 33 | 550 | 8.98 | 25.36 | 1.87 | 54.14 | 3.65 | 3.45 | 45.86 |
| 34 | 600 | 48.12 | 23.20 | 7.58 | 12.70 | 3.00 | 1.23 | 87.30 |
| 35 | 450 | 1.97 | 17.17 | 2.35 | 48.42 | 11.16 | 18.86 | 41.58 |
| 36 | 500 | 10.54 | 28.21 | 5.59 | 35.25 | 10.69 | 8.70 | 64.75 |
| 37 | 600 | 65.45 | 18.83 | 8.70 | 3.62 | 2.54 | — | 96.38 |

*TMP = trimethylphenol

EXAMPLES 38-41

The feedstock comprised 10 ml p-cresol in a 1.5:1 p-cresol/benzene solution and 10 ml of steam for Examples 38-41. A magnesium oxide catalyst containing 2 to 5 weight % manganese oxide and a polyphenylene oxide organic binder was utilized. The flow rates for both the steam and p-cresol was 0.35 ml per minute. Table IX provides the reaction temperatures utilized, and the products obtained in each of Examples 38-41. No dehydroxylated products were observed.

TABLE IX

| Ex. # | Temp. °C. | Phenol (g) | o-Cresol (g) | p-Cresol (g) | 2,6-Xylenol (g) | 2,4-Xylenol (g) | 2,4,6 TMP* Mesitol (g) |
|---|---|---|---|---|---|---|---|
| 38 | 450 | 24.32 | 9.21 | 55.01 | 0.80 | 9.97 | 0.74 |
| 39 | 500 | 33.69 | 8.67 | 41.00 | 2.51 | 10.26 | 1.39 |
| 40 | 550 | 19.09 | 2.47 | 71.12 | — | 6.25 | 0.26 |
| 41 | 600 | 19.47 | 1.77 | 68.56 | 0.45 | 6.68 | 0.69 |

*TMP = trimethylphenol

EXAMPLES 42-45

The feedstock utilized in Examples 42-45 comprised 10 ml of o-cresol in a 1.5:1 o-cresol/benzene solution and 10 ml of steam. The flow rate for both the steam and o-cresol was 0.35 ml per minute. The catalyst utilized comprised a magnesium oxide catalyst containing 2 to 5 weight % manganese oxide and a polyphenylene oxide organic binder. The reaction temperature utilized and the products obtained for each of their Examples are shown in Table X. No dehydroxylated products were observed.

TABLE X

| Ex. # | Temp. °C. | Phenol (g) | o-Cresol (g) | p-Cresol (g) | 2,6-Xylenol (g) | 2,4-Xylenol (g) | 2,4,6 TMP* (g) |
|---|---|---|---|---|---|---|---|
| 42 | 450 | 16.99 | 62.47 | 4.30 | 10.71 | 4.14 | 0.88 |
| 43 | 500 | 31.41 | 43.53 | 8.17 | 9.22 | 5.80 | 1.21 |
| 44 | 550 | 68.70 | 8.30 | 17.97 | 2.45 | 2.29 | 0.27 |
| 45 | 600 | 73.26 | 11.14 | 8.65 | 1.27 | 1.93 | — |

*TMP = trimethylphenol

EXAMPLES 46-49

The following Examples illustrate the effect of air on extending the life of the magnesium oxide catalyst in the processes comprising this invention. In each of Examples 46-49 the feedstock contained 2,4-xylenol which was passed over the catalyst at a rate of 0.2 LHSV. The feedstock for each of Examples 46-49 contained the following additional elements: Example 46—air (0.10 SCFH) and water (0.2 LHSV); Example 47—air (0.10 SCFH) without water; Example 48—nitrogen (0.10 SCFH) and water (0.2 LHSV); Example 49—nitrogen (0.10 SCFH) without water. These feedstocks were passed over a magnesium oxide catalyst with no promoter or organic binder at 500° C. The reaction products and degree of conversion obtained after one hour of operation are provided in Table XI. The products and degree of conversion obtained after four hours of operation are provided in Table XII. No dehydroxylation products were observed.

TABLE XI

| | | | One Hour Run | | | |
| Ex. # | Phenol (g) | o-Cresol (g) | p-Cresol (g) | 2,6-Xy-lenol (g) | 2,4-Xy-lenol (g) | 2,4,6 TMP* (g) | Conv. % |
|---|---|---|---|---|---|---|---|
| 46 | 2.23 | 9.82 | 12.95 | 5.45 | 46.56 | 22.95 | 53.44 |
| 47 | 2.13 | 10.50 | 13.12 | 5.63 | 44.05 | 24.57 | 55.95 |
| 48 | 0.88 | 4.12 | 14.77 | 1.07 | 58.25 | 20.90 | 41.75 |
| 49 | 0.00 | 1.99 | 16.51 | 0.00 | 65.98 | 15.50 | 34.02 |

TABLE XII

| | | | Four Hour Run | | | |
| Ex. # | Phenol (g) | o-Cresol (g) | p-Cresol (g) | 2,6-Xy-lenol (g) | 2,4-Xy-lenol (g) | 2,4,6 TMP* (g) | Conv. % |
|---|---|---|---|---|---|---|---|
| 46 | 2.27 | 9.90 | 14.20 | 3.21 | 47.00 | 23.42 | 53.00 |
| 47 | 0.00 | 2.73 | 12.15 | 0.78 | 64.23 | 20.11 | 35.77 |
| 48 | 0.00 | 0.00 | 3.77 | 0.00 | 90.05 | 6.18 | 9.95 |
| 49 | 0.00 | 0.00 | 0.67 | 0.00 | 97.25 | 2.08 | 2.75 |

*TMP = trimethylphenol

EXAMPLE 50

This example demonstrates the selectivity of the MgO catalysts. A feedstock comprised of 10 ml m-cresol and 10 ml of steam was passed over a MgO catalyst at a temperature of about 550° C. The flow rate for both steam and m-cresol was at 0.2 ml/minute.

Analysis of the condensate showed no change in the m-cresol started with.

Although the above Examples have shown various modifications of the present invention, further modifications are possible in light of the above techniques by one skilled in the art without departing from the scope and spirit of this invention.

What is claimed is:

1. A method of removing one or more alkyl radicals that are ortho or para positioned with respect to the hydroxyl radical of alkylated phenols with substantially no dehydroxylation comprising reacting an alkylated phenol with steam in the presence of a catalyst comprising magnesium oxide and an oxidizing atmosphere at a temperature in the range of about 400° to 675° C., said alkylated phenols having at least one alkyl radical either ortho-positioned or para-positioned to the hydroxyl radical, the alkyl radicals of said alkylated phenols having from 1 to 6 carbon atoms.

2. A process as in claim 1 wherein the oxidizing atmosphere is selected from the group consisting of air and oxygen.

3. A process as in claim 1 wherein the flow rate of alkylated phenols is within the range of 0.1 to 1.0 grams/hour/gram of catalyst.

4. A method as in claim 1 wherein the weight ratio of alkylated phenol to steam is in the range of about 1:1 to 1:15.

5. A method as in claim 1 wherein the reaction takes place under a pressure within the range of about 1 to 5 atmospheres.

6. A method as in claim 1 wherein the catalyst is comprised of about 80–90 weight % magnesium oxide, about 2 to 5 weight % manganese oxide and about 1 to 20 weight % of an organic binder.

7. A process as in claim 5 wherein the organic binder is polyphenylene oxide.

8. A process as in claim 6 wherein the flow rate of the oxidizing atmosphere provides a quantity of oxygen which gives a value for the ratio of moles oxygen/hour:moles alkylated phenol/hour within the range of about 1 to 5.

9. A process as in claim 8 wherein the oxidizing atmosphere is air.

10. A process as in claim 6 wherein the ratio of steam to alkylated phenols is within the range of 1:1 to 15:1.

11. A process as in claim 6 wherein the temperature is maintained within the range of about 450° to 550° C. and the pressure is maintained at about 1 atmosphere.

12. A process as in claim 6 wherein the flow rate of alkylated phenols is within the range of about 0.1 to 1.0 grams/hour/gram of catalyst.

13. A process as in claim 1 wherein the alkylated phenols are selected from the group consisting of o-cresol, p-cresol, 2,4-xylenol, 2,6-xylenol, 2,5-xylenol, 2,3-xylenol, 3,4-xylenol, 2,4,6-trimethylphenol, 2,3,5-trimethylphenol, 2,3,6-trimethylphenol, 2,3,4-trimethylphenol and 3,4,5-trimethylphenol.

14. A process as in claim 1 wherein the alkylated phenols are dissolved in an inert organic solvent.

15. A process as in claim 14 wherein the inert organic solvent is benzene.

16. A method of dealkylating alkylated phenols selected from the group consisting of 2,4-xylenol, 2,6-xylenol, 2,4,6-trimethylphenol, o-cresol and p-cresol with substantially no dehydroxylation; said method comprising reacting one or more of said alkylated phenols with steam in the presence of a catalyst comprising about 80–98 weight % magnesium oxide, 2 to 5 weight % manganese oxide and 1 to 10 weight % polyphenylene oxide in the presence of air at a temperature in the range of about 450° to 550° C., the ratio of alkylated phenol to steam falling within the range of about 1:0.5 to 1:5.

17. A method as in claim 16 wherein the flow rate of reactants falls within the range of about 0.1 to 1.0 grams/hour/gram of catalyst and the volume of air provides a value for the ratio of moles oxygen/hour:moles alkylated phenol/hour in the range of 1 to 5.

18. A process as in claim 16 wherein the organic binder is polyphenylene oxide.

19. A method of dealkylating 2,4,6-trimethylphenol with substantially no dehydroxylation wherein 2,4,6-trimethylphenol is reacted with steam in the presence of a catalyst comprised of 80-98 weight % magnesium oxide, 2 to 5 weight % manganese oxide and a polyphenylene oxide organic binder, said flow rate of 2,4,6-trimethylphenol falling within the range of about 0.1 to 1.5 LHSV, said ratio of steam to phenol falling within the range of about 0.5:1 to 15:1, said volume of air provides a value for the ratio moles oxygen/hour:moles alkylated phenol/hour in the range of 1 to 5, said temperature range falling within the range of about 500° to 575° C. and said pressure being at about 1 atmosphere.

20. A method of dealkylating 2,4-xylenol with substantially no dehydroxylation wherein 2,4-xylenol is reacted with steam in the presence of a catalyst comprised of magnesium oxide, 2 to 5 weight % manganese oxide and 1 to 20 weight % of a polyphenylene oxide organic binder, said flow rate of 2,4-xylenol falling within the range of about 0.1 to 1.0 grams/hour/gram of catalyst, said phenol to steam ratio falling within the range of about 1:0.5 to 1:15, said volume of air providing a value for the ratio moles oxygen/hour:moles alkylated phenol/hour in the range of 1 to 5, said temperature falling within the range of about 500° to 550° C. and said pressure being at about 1 atmosphere.

21. A method of transalkylating ortho and para positioned alkyl radicals of alkylated phenols to phenols having at least one ortho or para position vacant, said process comprising reacting in the vapor phase an alkyl radical donator consisting of an alkylated phenol having at least one alkyl radical at an ortho or para position with an alkyl radical acceptor consisting of a phenol having at least one ortho or para position vacant in the presence of an oxidizing atmosphere and a catalyst at a temperature in the range of about 400°–550° C., said alkyl radical having from 1 to 6 carbon atoms and said catalyst comprising about 80 to 90 weight % magnesium oxide, about 2–5 weight % manganese oxide and about 1–20 weight % organic binder.

22. A method as in claim 21 wherein the alkyl radical is a methyl group.

23. A method as in claim 21 wherein the organic binder is polyphenylene oxide.

24. A method as in claim 21 wherein said alkyl radical donator is selected from the group consisting of 2,4,6-trimethylphenol, 2,4-xylenol, 2,6-xylenol, o-cresol and p-cresol and said alkyl radical acceptor is selected from the group consisting of phenol, o-cresol, p-cresol, 2,4-xylenol and 2,6-xylenol.

25. A method as in claim 24 wherein said alkyl radical acceptor is different from said alkyl radical donator and the molar ratio of said alkyl radical acceptor to alkyl radical donator is within the range of 2:1 to 15:1.

* * * * *